United States Patent [19]

Gluchowski

[11] Patent Number: 5,237,072
[45] Date of Patent: Aug. 17, 1993

[54] METHOD FOR PRODUCING AMINO-2-IMIDAZOLINE DERIVATIVES

[75] Inventor: Charles Gluchowski, Mission Viejo, Calif.

[73] Assignee: Allergan, Inc., Irvine, Calif.

[21] Appl. No.: 855,211

[22] Filed: Mar. 20, 1992

Related U.S. Application Data

[62] Division of Ser. No. 475,842, Feb. 6, 1990, Pat. No. 5,130,441.

[51] Int. Cl.$^5$ .......................................... C07D 233/46
[52] U.S. Cl. .............................. 548/323.5; 548/331.5; 548/333.1
[58] Field of Search ................................ 548/351, 348

[56] References Cited

U.S. PATENT DOCUMENTS

| | | | |
|---|---|---|---|
| 1,912,849 | 6/1933 | Kranzlein et al. | 548/351 |
| 2,742,481 | 4/1956 | Cain | 548/351 |
| 2,876,223 | 3/1957 | Bloom | 260/256.4 |
| 3,890,319 | 7/1975 | Danielewicz et al. | 260/250 Q |
| 4,210,658 | 7/1980 | Durant et al. | 548/342 |
| 4,656,291 | 4/1987 | Maryanoff et al. | 548/351 |

FOREIGN PATENT DOCUMENTS

| | | |
|---|---|---|
| 2538620 | 8/1975 | Fed. Rep. of Germany . |
| 674018 | 1/1930 | France . |
| 407645 | 9/1966 | Switzerland . |

OTHER PUBLICATIONS

Clonidine and related compounds, Jarrott, Bevyn, Handbook of Hypertens., 1984, vol. 5, pp. 113–168.
Alpha 2-adrenergic agonists: a newer class of antidiarrheal drug, Dharmsathaphorn, K, Gastroenterology, Sep. 1986, 91, (3) pp. 769–770.
A Convenient Synthesis of Guanidines from Thioureas, Maryanoff et al, J. Org. Chem. (1986), pp. 1882–1884.
Alpha-2-adrenergic modulation of norepinephrine secretion in the perfused rabbit iris–ciliary body, Jumblatt et al, Curr. Eye Res., Jun. 1987, 6(6) pp. 767–777.
Ocular Effects of Selective alpha-adrenergic agents: A new drug paradox?, Mittag, Tom, Ann. Ophthalm. Mar. 1983 15(3) pp. 201–202.
Mechanism of alpha-2-adrenoceptor agonist-induced diuresis Gellai et al, Am J Physiol, Aug. 1988, 255(2 pt 2) pp 317–323.
Clonidine and some bridge analogs; cardiovascular effects and nuclear magnetic resonance data, Timmermans et al, Eur. J. Med. Chem., 1980 (15) pp 323–329.
Alpha 2-adrenergic receptors accelerate Na+/H+ exchange in neuroblastoma X Glioma Cells, Isom et al, J Biol Chem May 15, 1987, 262(14) pp. 6750–6757.
Clonidine:new research in psychotropic drug pharmacology, Fielding et al, Med Res Rev, Spring 1981, 1(1) pp. 97–123.
Renal effects of selective alpha-1 and alpha-2 adrenoceptor agonists in conscious, normotensive rats, Gellai et al, J. Pharmacol. Exp. Ther., Mar. 1987, 240(3) pp. 723–728.
Selective Alpha-2 adrenoceptor agonists alter fluid and electrolyte transport in mammalian small intestine, Fondacaro et al., J. Pharmacol. Exp. Ther., Nov. 1988, 247 (2) pp. 481–486.
Ocular effects of a relatively selective Alpha-2 agonist (UK-14,304-18) in cats, rabbit and monkeys, Burke et al, Curr. Eye Rsch,, Sep. 1986, 5(9), pp. 665–676.

*Primary Examiner*—David B. Springer
*Attorney, Agent, or Firm*—Gordon L. Peterson; Frank J. Uxa

[57] ABSTRACT

A method for producing an amino-2-imidazoline derivative comprises contacting an imidazoline sulfonic acid with at least one amine component in the presence of an alcohol-containing liquid medium at conditions effective to form the amino-2-imidazoline derivative.

20 Claims, No Drawings

METHOD FOR PRODUCING AMINO-2-IMIDAZOLINE DERIVATIVES

This application is a division of application Ser. No. 475,842, filed Feb. 6, 1990 now U.S. Pat. No. 5,130,441.

BACKGROUND OF THE INVENTION

The present invention relates to methods for producing amino 2-imidazoline derivatives. More particularly, the invention relates to methods for producing such derivatives which effectively provide high yields of the desired product or products.

Amino-2-imidazoline derivatives have a variety of uses including, but not limited to, as cardiovascular anti-hypertension agents; as sedatives and analgesics; as agents for the treatment of drug and alcohol withdrawal symptoms; as diuretic agents; as antidiarrheal agents; as agents which lower intraocular pressure and as vasoconstrictors.

Amino-2-imidazoline derivatives have been synthesized by a number of methods which include the reaction of ethylenediamine with an N-substituted-methylisothionium iodide salt or with an N-substituted dichloroimino derivative; the coupling of alkyl or aryl amines with N-acetyl-2-imidazolidinone in the presence of POCl$_3$ followed by hydrolysis of the intermediate N-acetyl imidazoline; and the. coupling of an alkyl or aryl amine with an S-alkyl-2-imidazoline. These methods have one or more drawbacks which include, for example, the use of harsh reagents such as POCl$_3$ which can react with sensitive functional groups substituted on the amine; the release of noxious by-products such as alkyl mercaptans; sensitivity to steric hinderance; and relatively complex, multi-step processing schemes.

Maryanoff et al U.S. Pat. No. 4,656,291 discloses a process for the production of guanidines by reaction of an amidine sulfonic acid with ammonia, or a primary or secondary amine, or a cyclic amine having an NH group in a solvent, such as water, acetonitrile or a dipolar aprotic solvent, at a temperature up to the boiling point of the solvent. Further, this patent discloses that the anti-hypertensive clonidine, i.e., 2-(2,6-dichlorophenylamino)-2-imidazoline, can be synthesized by reacting the appropriate amidine sulfonic acid with ethylenediamine. The amidine sulfonic acid is produced by oxidizing a thiourea with hydrogen peroxide in the presence of a molybdenum catalyst at temperatures in the range of about 0° C. to 80° C., with a final oxidation temperature of about 15° C. to 80° C.

More effective, e.g., less hazardous and/or more economic, methods for producing amino-2-imidazoline derivatives would be advantageous. For example, increased yields of the desired derivative or derivatives would be a particularly useful benefit since overall processing would be reduced and the amounts of unwanted by-products would be decreased.

SUMMARY OF THE INVENTION

A new method for the production of amino-2-imidazoline derivatives has been discovered. This method provides substantial benefits relative to previously used or suggested production methods. For example, the starting materials, intermediates, liquid media, and catalysts used are relatively easy to handle and to dispose of, if necessary. Importantly, the present method provides outstandingly high yields of the desired product or products so that substantial process efficiencies are achieved.

In one broad aspect, the present invention provides a method for the production of an amino-2-imidazoline derivative which includes contacting an imidazoline sulfonic acid with at least one amine component in the presence of a liquid medium, preferably a solvent, at conditions effective to form the amino-2-imidazoline derivative. The amine component is selected from the group consisting of primary amines, primary amine salts, secondary amines, secondary amine salts and mixtures thereof. Substantial benefits, e.g., high yields of the desired amine-2-imidazoline derivative, are achieved utilizing at least one alcohol as at least a portion of the liquid medium.

The imidazoline sulfonic acid is preferably produced by a method which includes contacting a thiourea and hydrogen peroxide in the presence of a molybdenum-containing component at conditions effective to oxidize the thiourea to the imidazoline sulfonic acid. Substantial benefits, e.g., high yields of the desired imidazoline sulfonic acid, are achieved by conducting substantially all of the thiourea oxidizing at a temperature of less than 0° C., more preferably in the range of about −20° C. to about −5° C.

In addition, a new compound has been discovered. This compound has the formula

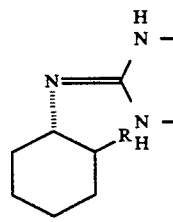

where R is an alkyl radical containing 1 to about 5 carbon atoms, preferably an ethyl group. This compound is effective when administered to a mammalian eye, particularly a mammalian eye effected with glaucoma, to reduce or maintain the intraocular pressure in the mammalian eye.

DETAILED DESCRIPTION OF THE INVENTION

The presently produced amino-2-imidazoline derivatives have the following generalized formula

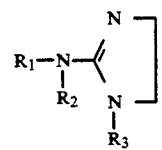

where $R_1$ is a monovalent hydrocarbon radical, a monovalent substituted hydrocarbon radical, a heterocyclic radical or a monovalent substituted heterocyclic radical; and $R_2$ and $R_3$ are independently selected from H, a monovalent hydrocarbon radical, a monovalent substituted hydrocarbon radical, a monovalent heterocyclic radical or a monovalent substituted heterocyclic radical. $R_1$ and $R_2$ may be joined together, e.g., in a ring structure. $R_1$ is preferably selected from alkyl, substituted alkyl, alkenyl, substituted alkenyl, aryl, substituted aryl, heterocyclic and substituted heterocyclic.

More preferably, $R_1$ includes up to about 20 carbon atoms, still more preferably up to about 14 carbon atoms. Both $R_2$ and $R_3$ may be H. If $R_2$ or $R_3$ is other than H, such radical is preferably selected from alkyl, substituted alkyl, alkenyl, substituted alkenyl, aryl, substituted aryl, heterocyclic and substituted heterocyclic; more preferably including up to about 20 carbon atoms, still more preferably up to about 14 carbon atoms. When $R_2$ is H, the derivatives can exist in the following tautomeric forms

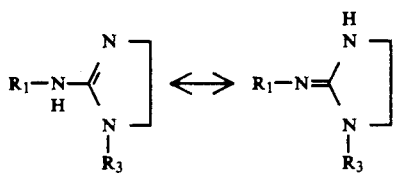

As used herein, the term amino-2-imidazoline derivative includes either one or both of these tautomeric forms. Also, such term refers to any of the stereoisomers and mixtures thereof which comply with the constraints of one of the formulae set forth herein for such amino-2-imidazoline derivatives.

These amino-2-imidazoline derivatives are produced by a method which comprises contacting an imidazoline sulfonic acid with at least one amine component in the presence of an alcohol-containing liquid medium, preferably an alcohol-containing solvent.

The imidazoline sulfonic acid can exist in the following tautomeric forms

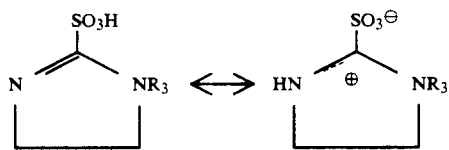

wherein $R_3$ is as described herein. As used herein, the term imidazoline sulfonic acid refers to either one or both of these tautomeric forms, and to any of the stereoisomers and mixtures thereof which comply with the constraints of one of the formulae set forth herein for the imidazoline sulfonic acid.

The amine component is selected from primary amines, primary amine salts, secondary amines, secondary amine salts and mixtures thereof. Any and all tautomers, steriosomers and mixtures thereof of such amine components are included.

The amine component preferably has the formula $$R_1-NH$$
$$|$$
$$R_2$$

and salts thereof, wherein $R_1$ and $R_2$ are as described herein. The amine component may include more than one $NH_2$ (amino) group. More preferably, the amine component is selected from the group consisting of primary amines, primary amine salts and mixtures thereof.

Among the amine salts useful in the present invention are those containing anions, such as the hydrochloride, hydrobromide, hydrocodide, sulfate or bisulfate, phosphate or acid phosphate, acetate maleate, fumarate, oxalate, lactate, tartrate, citrate, gluconate, saccharate and p-toluene sulfonate salts.

When an acid amine salt is used as all or part of the amine component, the contacting may be benefited by the presence of one or more tertiary amines, in particular one or more tertiary alkyl or trialkyl amines, for example, tertiary alkyl amines containing 3 to about 20 carbon atoms. Each of the alkyl radicals or groups included in the tertiary alkyl amine may be the same or different relative to the other of such alkyl radicals or groups. Triethylamine is a particularly useful tertiary amine. The tertiary amine is preferably present in an amount effective to result in the formation of the amine from the amine acid salt. In a particularly useful embodiment, the amount of tertiary amine used, in equivalents, is about equal to the number of equivalents of the amine acid salt present.

At least a portion, preferably a major amount and more preferably substantially all, of the liquid medium is at least one alcohol. As used herein, the term alcohol refers to a compound having the formula $$R_4OH$$

wherein $R_4$ is selected from monovalent hydrocarbon radicals and monovalent substituted hydrocarbon radicals, preferably containing 1 to about 10 carbon atoms. $R_4$ may include one or more hydroxyl groups. The presently useful alcohols can contain 1 or more, preferably 1 to about 3, hydroxyl groups. More preferably, the alcohol contains only one hydroxyl group. The alcohol is preferably an alkanol, i.e., where $R_4$ is an alkyl radical or an alkyl radical substituted with one or more hydroxyl groups. The number of carbon atoms present in the alcohol is more preferably 1 to about 5. Examples of useful alcohols include methanol, ethanol, isopropanol, isobutanol, mixtures thereof and the like. A particularly useful alcohol is isobutanol.

The amount of liquid medium employed is preferably sufficient to completely dissolve the amounts of imidazoline sulfonic acid and amine component being contacted. In such instances, the liquid medium acts as a solvent for the imidazoline sulfonic acid and amine component being contacted. Large excesses of solvent are to be avoided since such amounts can result in increased processing and purification time and costs, and in increased materials handling.

The liquid medium may include one or more other components which are compatible with the alcohol or alcohols used, and which do not have any substantial detrimental effect on the imidazoline sulfonic acid/amine component contacting. Examples of such other components include water, acetonitrile and the like. Very good results are obtained when the alcohol or alcohols comprise substantially al of the liquid medium.

As used herein, "hydrocarbon radical" is any radical made up of carbon and hydrogen atoms; "alkyl" is any saturated non-aromatic hydrocarbon radical; "alkenyl" is any unsaturated non-aromatic hydrocarbon radical; "aryl" is any hydrocarbon radical having an available bonding site on an aromatic hydrocarbon ring; "heterocyclic" is any radical including a ring having at least one carbon atom and at least one heteroatom (an atom other than a carbon atom), such as N, S, O and the like; and "substituted" is any of such radicals where one or more hydrogen atoms are replaced by one or more other species including, but not limited to: monovalent hydrocarbon radicals, such as alkyl, alkenyl and aryl;

heterocyclic radicals; halogen, such as F, Cl, Br and I; NH₂; NO₂; OH; alkoxy; alkythio; aryloxy; arylthio; alkanoyl; alkanoyloxy; aroyl; aroyloxy; acido; amido; alkylamino; dialkylamino; arylamino; alkylarylamino; diarylamino; alkanoylamino; alkylsulfinyl; alkylsulfenyl; aklysufonyl; alkylsulfonylamido; azo; benzyl; carboxy; cyano; guanyl; guanidino; imino; phosphinyl; phosphorus; silyl; thioxo; ureido or vinylidene or where one or more carbon atoms are replaced by one or more other species including, but not limited to: O or S.

In another important aspect of the present invention, the presently useful imidazoline sulfonic acid is produced by contacting the corresponding thiourea with hydrogen peroxide in the presence of molybdenum-containing component, in particular initially in the presence of a molybdenum (VI)-containing component, at conditions effective to oxidize the thiourea and form the imidazoline sulfonic acid. The contacting conditions include a temperature of less than 0° C., preferably in the range of about −20° C. to about −5° C.. Substantially all of the thiourea oxidation preferably occurs at these temperatures. Such temperatures are reduced relative to the temperatures suggested in the prior art and result in substantial benefits, e.g., high yields of the desired imidazoline sulfonic acid.

The thiourea which is oxidized in accordance with the present invention has the following formula

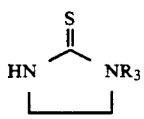

wherein R₃ is as described herein. A particularly useful thiourea has the following formula

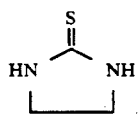

During the reaction, the oxidation state of the molybdenum may vary. For example, when an Mo (VI) component is used, the oxidation state of the molybdenum can change from (VI) to (III) to (O). The molybdenum-containing component employed is preferably one or more molybdates of the formula QMoO₄ wherein Q is two ions each having a +1 valence or one ion having a +2 valence. Specific examples of molybdenum components include H₂MoO₄, (NH₄)₂MoO₄ and alkali metal, in particular sodium, molybdates. Molybdate hydrates (and other solvates) may be employed as the molybdenum-containing component. The amount of molybdenum-containing component used is not critical to the present invention. Sufficient molybdenum-containing component is preferably present to at least facilitate, e.g., promote, the oxidation reaction. The molybdenum containing component may act to at least partially oxidize the thiourea. The amount of such component may be, and preferably is, substantially less than the stoichiometric amount, i.e., that amount required to completely oxidize the thiourea to the amidine sulfonic acid if no other source of active oxygen is present. In one embodiment, the amount of molybdenum-containing component used is in the range of about 1% to about 50% of the stoichiometric amount.

Hydrogen peroxide is used, preferably as an aqueous solution, such as an aqueous solution containing about 10% to about 90%, e.g., a 30%, (w/v) of hydrogen peroxide. Other peroxide sources, such as peracetic acid, can be used. The amount of peroxide used is not critical to the present invention provided sufficient active oxygen is present to provide the desired thiourea oxidation. In one embodiment, the amount of peroxide used is in the range of about 50% to about 150% or more of the stoichiometric amount.

The thiourea oxidation preferably takes place in the presence of a liquid, more preferably an aqueous liquid. The composition of this liquid is preferably such as not to have any substantial detrimental effect on the thiourea oxidation. Water is a useful liquid in the thiourea oxidation.

A new compound having the formula

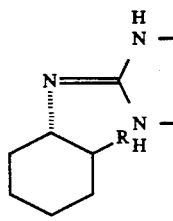

wherein R₃ is an alkyl radical, preferably containing 1 to about 5 carbon atoms, such as a methyl radical a ethyl radical, a propyl radical, a butyl radical or a pentyl radical, and in particular an ethyl radical, can be prepared with the present methods. This compound can exist in the following tautomeric forms.

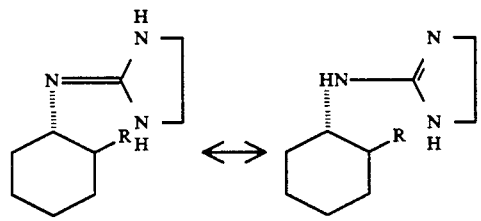

Either one or both of these tautomeric forms is hereinafter represented by the formula for the first tautomeric form noted above.

This new compound has been found to be effective in reducing or maintaining intraocular pressure in mammalian eyes, e.g., effected by glaucoma. Thus, this compound is effective in the management or treatment of glaucoma.

The new compound is often administered to the eye of a mammal to reduce or maintain intraocular pressure in the form of a mixture with an ophthalmically acceptable carrier. Any suitable, e.g., conventional, ophthalmically acceptable carrier may be employed. Such a carrier is ophthalmically acceptable if it has substantially no long term or permanent detrimental effect on the eye to which it is administered. Examples of ophthalmically acceptable carriers include water, in particular distilled water, saline and the like aqueous media. The present compounds are preferably administered to the eye as a liquid mixture with the carrier. The compounds are more preferably soluble in the carrier so that the compounds are administered to the eye in the form of a solution.

When an ophthalmically acceptable carrier is employed, it is preferred that the mixture contain one or more of the new compounds in an amount in the range of about 0.0001% to about 1%, more preferably about 0.05% to about 0.5%, w/v.

Any method of administering drugs to a mammalian eye may be employed to provide the new compound or compounds to the eye to be treated. Preferably, the compound or compounds are provided by being administered directly to the eye being treated. By the term "administered directly" is meant to exclude those general systemic drug administration modes, e.g., injection directly into the patients blood vessels, oral administration and the like, which result in the compound or compounds being systemically available. The primary effect on the mammal resulting from the direct administering of the present compound or compounds to the mammal's eye is preferably a reduction in intraocular pressure. More preferably, the present compound or compounds are applied topically to the eye or are injected directly into the eye. Particularly useful results are obtained when the compound or compounds are applied topically to the eye.

Topical ophthalmic preparations, for example ocular drops, gels or creams, are preferred because of ease of application, ease of dose delivery, and fewer systemic side effects. An exemplary topical ophthalmic formulation is shown below in Table I. The abbreviation q.s. means a quantity sufficient to effect the result or to make volume.

TABLE I

| Ingredient | Amount (% W/V) |
|---|---|
| Present amino-2-imidazoline derivative | about 0.0001 to about 1.0 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include, but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetycysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

The following non-limiting examples illustrate certain aspects of the present invention.

EXAMPLE 1

Synthesis of Imidazoline-2-sulfonic acid

2-Imidazolidinethione (66.3 g, 650 mmol), $Na_2MoO_4$ (5g, 227 mmol) and NaCl (15 g. 256 mmol) were added to 300 ml $H_2O$. Although some dissolution occurred, a solid residue remained in the liquid of the mixture. The mixture was cooled to $-10°$ C. using an immersion cooler. 500 ml of a 30% (w/v) aqueous $H_2O_2$ solution was placed in a jacketed controlled drip rate addition funnel and cooled to $0°$ C. using an ice/$H_2O$ bath. The aqueous $H_2O_2$ solution was added to the mixture at a rate of 60 drops/min. The mixture was stirred for 16 hours at $-10°$ C. During this time, the mixture changed from a white suspension to a dark blue solution to a light blue suspension. At the end of 16 hours, a solid was filtered from the suspension and dried in vacuo. No further purification was needed. 57.8 g (a yield of 52.3%) of the title compound as a white solid, which was characterized spectroscopically, was recovered. This solid was stable when stored in the dark at $O°$ C. for at least 6 months.

EXAMPLE 2

Synthesis of Clonidine (2-(2,6-dichlorophenylamino)-2-imidazoline)

A mixture of 2,6-dichloroaniline (0.162 g, 1 mmol), imidazoline-2-sulfonic acid (0.30 g, 2 mmol) and isobutanol (3 ml) was heated to 125° C. and maintained at this temperature for 16 hours. The mixture was then cooled to room temperature, diluted with $CHCl_3$ (10 ml) and washed twice with 2 ml of aqueous 1 N NaOH. The organic extracts were combined, dried over $MgSO_4$ and concentrated in vacuo to yield a solid which was chromatographed (silica gel, 10:1 $CHCl_3/CH_3OH$ saturated with $NH_3$ (g)) to yield 0.147 g (a yield of 64%) of the title compound as a white solid, which was characterized spectroscopically.

EXAMPLE 3

Synthesis of 5-Bromo-6-(2-imidazolin-2-ylamino)-quinoxaline

A mixture of 6-amino-5-bromo quinoxaline (prepared using the method reported by Danielewicz U.S. Pat. No. 3,890,319) (0.224 g, 2 mmol), imidazoline-2-sulfonic acid (0.30 g, 2 mmol) and isobutanol (3 ml) was heated to 125° C. and maintained at this temperature for 16 hours. The mixture was then cooled to room temperature and concentrated in vacuo to give a brown residue which was chromatographed (silica gel, 9:1 $CHCl_3/CH_3OH$ saturated with $NH_3$ (g)) to yield 0.177 g (a yield of 61%) of the title compound as a yellow solid, which was characterized spectroscopically.

EXAMPLE 4

Synthesis of 2-(trans-2-hydroxycyclohexylamino)-2-imidazoline

A mixture of trans-1-aminocyclohexanol (0.115 g, 1.0 mmol), imidazoline-2-sulfonic acid (0.30 g, 2 mmol) and isobutanol (3 ml) was heated to 50° C. and maintained at that temperature for 7 hours. The mixture was then cooled to room temperature, concentrated in vacuo and chromatographed (silica gel, 2:1 CHCl₃/CH₃OH saturated with NH₃(g)) to yield 0.134 g (a yield of 73%) of the title compound as a white solid, which was characterized spectroscopically.

EXAMPLE 5

Synthesis of 2-(2-4-morpholinyl)-2-imidazoline

A mixture of morpholine (0.174 g, 2 mmol), imidazoline-2-sulfonic acid (0.30 g, 2 mmol) and isobutanol (3 ml) was heated to 50° C. and maintained at that temperature for 2 hours. The mixture was then cooled to room temperature, concentrated in vacuo and the residue chromatographed (silica gel, 5:1 CHCl₃/CH₃OH saturated with NH₃ (g)) to yield 0.075 g (a yield of 25%) of the title compound as a white solid, which was characterized spectroscopically.

EXAMPLE 6

Synthesis of 2-(trans-2-ethylcyclohexylamino)-2-imidazoline

A mixture of trans-2-ethylcyclohexylamine hydrochloride (0.30 g, 2.36 mmol), imidazoline-2-sulfonic acid (0.704 g, 4.72 mmol) and isobutanol (3 ml) was heated to 125° C. and maintained at that temperature for 2 hours. The mixture was cooled to room temperature, concentrated in vacuo and chromatographed (silica gel, 3:1 CHCl₃/CH₃OH saturated with NH₃ (g)) to yield 0.253 g (a yield of 65%) of the title compound as a white solid, which was characterized spectroscopically.

EXAMPLE 7

2-(trans-2-ethylcyclohexylamino)-2-imidazoline produced in accordance with Example 6 is tested to determine what effect this material has on intraocular pressure.

This material is dissolved in distilled water at a concentration of 0.1% (w/v). The solution is administered topically and unilaterally to one eye of a drug-naive, unanesthetized New Zealand white rabbit in a single 50 micro liter drop. The contralateral eye receives an equal volume of saline prior to determining the intraocular pressure after the mixture was administered. Also, approximately 10 micro liters of 0.5% (w/v) proparacaine (topical anesthetic) is applied to the corneas of the rabbit before determining intraocular pressure.

The intraocular pressure is determined in both eyes of the rabbit before and after the solution is administered. Such intraocular pressure determinations are made in the conventional manner using conventional equipment.

Results of this test indicate that the 2-(trans-2-ethylcycloamino)-2-imidazoline effectively reduces intraocular pressure in mammalian eyes.

EXAMPLES 8 TO 14

A series of experiments were run to determine the effect of solvent on product yield from the following reaction:

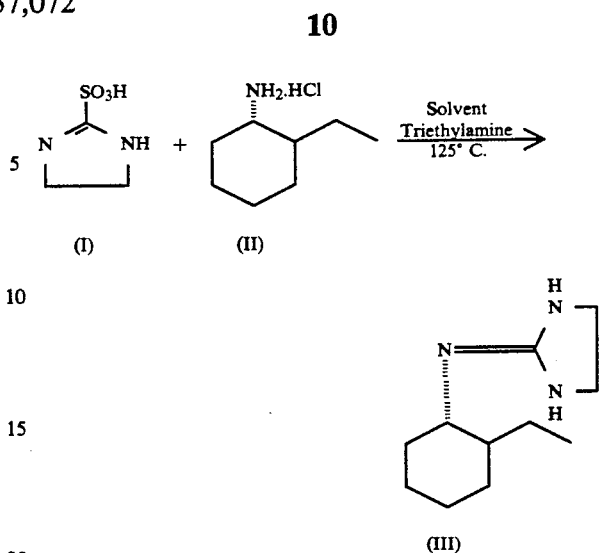

Each experiment was run as follows. 0.704 g of (I) and 0.30 g of (II) were dissolved in 3 ml of a particular solvent. 0.24 g of triethylamine was added to the solution, which was then heated to 125° C. and maintained at that temperature for 2 hours. After this time, the solution was cooled and an amount of (III) was recovered. The % yield was determined by weighing the amount of (III) actually recovered in any one experiment and calculating the theoretical amount of (III) which could be produced in such experiment. The ratio of the former to the latter multiplied by 100 provides the % yield.

Results of these tests were as follows:

| Example | Solvent | % Yield Of (III) |
|---|---|---|
| 8 | H₂O | 0 |
| 9 | CH₃CN | 18–20 |
| 10 | H₂O:CH₃CN(3:2 by volume) | 10–12 |
| 11 | CH₃OH | 20–25 |
| 12 | CH₃—CH₂—OH | 20–27 |
| 13 | (CH₃)₂—CH—OH | 40–42 |
| 14 | (CH₃)₂—CH₂—CH₂—OH | 57–65 |

These results demonstrate that alcohol, in particular alkanol, solvents unexpectedly provide for increased yields of desired products relative to solvents such as water and acetonitrile. This is indeed surprising since water and acetonitrile have been suggested as useful solvents for this type of reaction. Also note the particularly outstanding results achieved with isobutanol solvent. The reaction takes place in isobutanol solvent with or without triethylamine being present.

While this invention has been described with respect to various specific examples and embodiments, it is to be understood that the invention is not limited thereto and that it can be variously practiced within the scope of the following claims.

What is claimed is:

1. In a method for the production of an imidazoline sulfonic acid which includes oxidizing a thiourea in the presence of hydrogen peroxide and a molybdenum-containing component at conditions effective to form said imidazoline sulfonic acid, the improvement which comprises conducting substantially all of said oxidizing at a temperature of less than 0° C.

2. The method of claim 1 wherein said thiourea has the formula

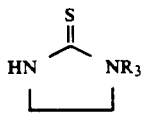

wherein $R_3$ is selected from the group consisting of H, monovalent hydrocarbon radicals, monovalent substituted hydrocarbon radicals, monovalent heterocyclic radicals and monovalent substituted heterocyclic radicals.

3. The method of claim 1 wherein said thiourea has the formula

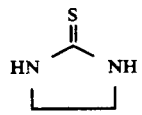

4. The method of claim 1 wherein said temperature is in the range of about $-20°$ C. to $-5°$ C.

5. In a method for producing an amino-2-imidazoline derivative including the steps of:

contacting a thiourea having the following formula

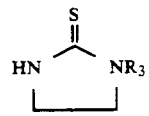

wherein $R_3$ is selected from the group consisting of H, monovalent hydrocarbon radicals, monovalent substituted hydrocarbon radicals, monovalent heterocyclic radicals and monovalent substituted heterocyclic radicals, hydrogen peroxide, and an amount of molybdenum-containing component effective to at least facilitate the oxidation of said thiourea, said contacting occurring at conditions effective to oxidize said thiourea and form an imidazoline sulfonic acid having the following formula

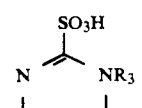

; and contacting said imidazoline sulfonic acid with an amine component selected from the group consisting of primary amines, primary amine salts, secondary amines, secondary amine salts and mixtures thereof in the presence of a liquid medium at conditions effective to form an amino-2-imidazoline derivative having the following formula

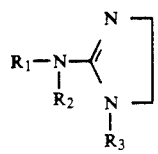

wherein $R_1$ is selected from the group consisting of monovalent hydrocarbon radicals, monovalent substituted hydrocarbon radicals, monovalent heterocyclic radicals and monovalent substituted heterocyclic radicals; and $R_2$ is selected from the group consisting of H, monovalent hydrocarbon radicals, monovalent substituted hydrocarbon radicals, monovalent heterocyclic radicals and monovalent substituted heterocyclic radicals, the improvement comprising including in said liquid medium an alcohol selected from the group consisting of secondary alcohols, tertiary alcohols and mixtures thereof.

6. The method of claim 5 wherein said alcohol contains 1 and about 3 hydroxyl groups, and up to about 10 carbon atoms.

7. The method of claim 6 wherein said alcohol contains only 1 hydroxyl group.

8. The method of claim 7 wherein said alcohol contains up to about 5 carbon atoms.

9. The method of claim 5 wherein said alcohol is isobutanol.

10. The method of claim 5 wherein said amine component is selected from the group consisting of primary amines, primary amine salts and mixtures thereof, and said reaction takes place in the presence of a tertiary amine.

11. The method of claim 10 wherein said tertiary amine is selected from the group consisting of trialkyl amines containing 3 to about 20 carbon atoms and mixtures thereof.

12. The method of claim 11 wherein said tertiary amine is triethylamine.

13. The method of claim 5 wherein said alcohol is at least a major amount of said liquid medium.

14. The method of claim 5 wherein said alcohol is substantially all of said liquid medium.

15. The method of claim 5 wherein said imidazoline sulfonic acid/amine component contacting takes place at a temperature in the range of about $40°$ C. to about $200°$ C.

16. The method of claim 5 wherein said amine component has the following formula

and salts thereof wherein $R_1$ is selected from the group consisting of monovalent hydrocarbon radicals, monovalent substituted hydrocarbon radicals, monovalent heterocyclic radicals and monovalent substituted heterocyclic radicals; and $R_2$ is selected from the group consisting of H, monovalent hydrocarbon radicals, monovalent substituted hydrocarbon radicals, monovalent heterocyclic radicals and monovalent substituted heterocyclic radicals.

17. The method of claim 5 wherein said conditions effective to form an imadazoline sulfonic acid include a temperature below about $0°$ C.

18. The method of claim 5 wherein said conditions effective to form an imidazoline sulfonic acid include a temperature in the range of about $-20°$ C. to about $-5°$ C.

19. The method of claim 5 wherein said molybdenum-containing component is a molybdenum (VI)-containing component.

20. The method of claim 16 wherein said imidazoline sulfonic acid has the following formula
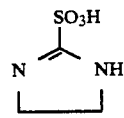
and $R_2$ is H.
* * * * *